(12) United States Patent
Scheiflinger et al.

(10) Patent No.: US 8,795,999 B2
(45) Date of Patent: Aug. 5, 2014

(54) IMMUNOADSORPTION OF ANTI-VON WILLEBRAND FACTOR CLEAVING PROTEASE ANTIBODIES

(75) Inventors: Friedrich Scheiflinger, Vienna (AT); Barbara Plaimauer, Vienna (AT); Gerhard Antoine, Gross Enzersdorf (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 317 days.

(21) Appl. No.: 12/388,450

(22) Filed: Feb. 18, 2009

(65) Prior Publication Data

US 2009/0264631 A1 Oct. 22, 2009

Related U.S. Application Data

(62) Division of application No. 10/395,900, filed on Mar. 20, 2003, now abandoned.

(51) Int. Cl.
| | |
|---|---|
| *C12N 5/07* | (2010.01) |
| *C12N 5/16* | (2006.01) |
| *C12N 7/02* | (2006.01) |
| *C12N 11/00* | (2006.01) |
| *C12N 13/00* | (2006.01) |

(52) U.S. Cl.
USPC .......... 435/173.9; 435/7.1; 435/7.2; 435/174; 435/239; 435/287.2; 435/331; 435/337; 435/344.1

(58) Field of Classification Search
None
See application file for complete search history.

(56) References Cited

U.S. PATENT DOCUMENTS

| | | | |
|---|---|---|---|
| 5,854,403 A | 12/1998 | Fischer et al. | |
| 6,414,125 B1 | 7/2002 | Siekmann et al. | |

FOREIGN PATENT DOCUMENTS

| | | | | |
|---|---|---|---|---|
| EP | 1 609 804 A1 | 12/2005 | | |
| WO | WO 96/10584 | 4/1996 | | |
| WO | WO 02/42441 A2 | * 5/2002 | ............... | C12N 9/64 |
| WO | WO 03/009887 A2 | 2/2003 | | |

OTHER PUBLICATIONS

Gerritsen et al., (Blood. 2001. vol. 98(6):1654-1661).*
Kavanagh et al., (Thromb Haemost. 1981 45(1): 60-4) a.*
Fisher et al., Biochemical Society Transactions. 1987. vol. 16:134-138).*
Soff et al., (J Lab Clin Med. Mar. 1993. 121(3):424-30).*
Fujikawa et al., *Blood* 98(6): 16562-1666.
Furlan et al., "Partial purification and characterization of a protease from human plasma cleaving von Willebrand Factor to fragments produced by in vivo proteolysis," *Blood* (1996) 87: 4223-4234.
Furlan et al., Acquired deficiency of von Willebrand Factor-cleaving protease in a patient with thrombotic thrombocytopenic purpura, *Blood* (1998) 91: 2839-2846.
Furlan et al., "von Willebrand Factor—cleaving protease in thrombotic thrombocytopenic purpura and the hemolytic-uremic syndrome," *The New England Journal of Medicine* (1998) 339: 1578-1584.
Gerritsen et al., "Partial amino acid sequence of purified von Willebrand Factor-cleaving protease," *Blood* (2001) 98(6): 1654-1661.
Hinman and Stevens-Truss, "In-line affinity Chromatographic removal of specific antibody from rabbits with experimental myastheniz gravis as a prelude to immunotherapy," *Immunopharmacology and Immunotoxicology* (1998) 20(2): 233-249.
Kadar and Borberg, "Biocompatibility of extracorporeal immunoadsorption systems," *Transfus. Sci.* (1990) 11: 223-239.
Pietu et al., "Epitope mapping by cDNA expression of a monoclonal antibody which inhibits the binding of von Willebrand Factor to platelet glycoprotein IIb/IIIa," *Biochem. J.* (1992) 284: 711-715.
Plaimauer et al., "Cloning, expression, and functional characterization of the von Willebrand Factor-cleaving protease (ADAMTS13)," *Blood* (Nov. 15, 2002) 100(10): 3626-3632.
Stewart et al., "vWf inhibitor detection by competitive ELISA," *J. of Immunological Methods* (1997) 200: 113-119.
Takamori and Ide, "Specific removal of antiacetylcholine receptor antibodies in patients with myasthenia gravis," *Transfus. Sci.* (1996) 17(3): 445-453.
Van Genderen et al., "Acquired von Willebrand disease caused by an autoantibody selectively inhibiting the binding of v on Willebrand factor to collagen," *Blood* (1994) 84(10): 3378-3384.
Williams et al., "Production and functional activity of a recombinant von Willebrand factor-A domain from human complement factor B," *Biochem. J.* (1999) 342: 625-632.
Zheng et al., "Structure of von Willebrand Factor-cleaving protease (ADAMTS13), a metalloprotease involved in thrombotic thrombocytopenic purpura," *J. Biol. Chem.* (2001) 276: 41059-41063.

* cited by examiner

*Primary Examiner* — Ja'na Hines
(74) *Attorney, Agent, or Firm* — Kilpatrick Townsend & Stockton LLP (57) ABSTRACT

This invention relates to adsorbents and methods for highly selective removal of anti-von Willebrand Factor-cleaving protease antibodies ("anti-vWF-cp-abs") from human plasma using human von Willebrand Factor-cleaving protease ("hvWF-cp") or fragments thereof as affinity ligands. The adsorbents can be used for treating disorders associated with the occurrence of anti-vWF-cp-abs in patients, such as thromboembolic diseases.

15 Claims, 4 Drawing Sheets

IMMUNOADSORPTION OF ANTI-VON WILLEBRAND FACTOR CLEAVING PROTEASE ANTIBODIES

CROSS-REFERENCE TO RELATED APPLICATIONS

This application is a divisional application of U.S. application Ser. No. 10/395,900, filed Mar. 20, 2003, now abandoned, which application is herein incorporated by reference.

FIELD OF THE INVENTION

This invention relates to adsorbents and methods for highly selective removal of anti-von Willebrand Factor-cleaving protease antibodies ("anti-vWF-cp-abs") from human plasma using human von Willebrand Factor-cleaving protease ("hvWF-cp") or fragments thereof as affinity ligands. The adsorbents can be used for treating disorders associated with the occurrence of anti-vWF-cp-abs in patients, such as thromboembolic diseases.

BACKGROUND

The von Willebrand Factor-cleaving protease is involved in the limitation of platelet thrombus growth by proteolytic cleavage of von Willebrand Factor multimers in man (Furlan et al., Blood 1996, 87: 4223-4234). Recently, the molecular structure of von Willebrand Factor-cleaving protease and the corresponding gene have been described (WO 02/42441; Zheng et al., J. Biol. Chem. 2001, 276: 41059-41063).

A deficiency of von Willebrand Factor-cleaving protease could cause severe disorders such as acquired thrombotic thrombocytopenic purpura or hemolytic-uremic syndrome. One reason for such a deficiency of von Willebrand Factor-cleaving protease is the occurrence of autoantibodies which inhibit the von Willebrand Factor-cleaving protease (Furlan et al., Blood 1998, 91: 2839-2846; Furlan et al., N Engl J Med 1998, 339: 1578-1584). So far, such autoantibodies can be removed from a patient's plasma by protein A immunadsorption. However, the main disadvantage of protein A immunadsorption is its low selectivity, i.e. essentially no discrimination against immunoglobulin isotypes.

SUMMARY

An object of the present invention is to provide an improved adsorbent for highly selective removal of anti-vWF-cp-abs from human plasma. The adsorbent comprises hvWF-cp or fragments thereof, coupled to an inert matrix material, said hvWF-cp or fragments thereof having at least one functionally active epitope directed to said anti-vWF-cp-abs under physiological conditions.

Another object of the present invention is to provide a method for highly selective removal of anti-vWF-cp-abs from human plasma using the above-defined adsorbent. In particular, the method comprises the steps of:

(a) providing plasma from whole blood of a patient having a disorder associated with occurrence of anti-vWF-cp-abs;
(b) subjecting said plasma to an affinity chromatography using the above-defined adsorbent; and
(c) collecting the flow-through fraction which is essentially devoid of anti-vWF-cp abs.

DETAILED DESCRIPTION

A variety of matrix materials can be used in the adsorbent of the present invention as long as it is inert. In this respect the term "inert" means that the matrix material does not have any negative impact on the different fluids used in affinity chromatography, such as human plasma, binding buffers, regeneration buffers, or storage buffers. Specific examples of suitable matrix materials include, but are not limited to, carbohydrates such as cross-linked modified agarose, silicates, glasses, and organic polyreaction products including polymers or copolymers. The matrix material may be present in any form such as spherical, planar or fibrous, and may be porous or non-porous. In certain embodiments of the present invention, the matrix material is present in the form of porous beads. Further, the matrix material is typically biocompatible, and additionally, exhibits substantially no leakage. Examples of solid matrix material for ligand immobilisation include polymers such as agarose (e.g., NHS-, CNBr-, Epoxy-activated Sepherose®, EAH Sepharose®, commercially available from Amersham Pharmacia); Affi-Gel (commercially available form Bio-rad); cellulose (e.g., Cellufine, commercially available from Millipore); polystyrene (e.g., activated Poros Media, commercially available from Perseptive Biosystems); Mono Q; Source; and activated affinity resins (e.g., TSK gel ABA-, Boronate-, Chelate-, and Tresyl-5PW, commercially available from Tosoh Biosep).

For coupling the affinity ligand to the matrix material, the affinity ligand can be directly coupled onto the matrix material via a chemical reaction or indirectly coupled onto the matrix material using a spacer. In certain embodiments of the present invention, the affinity ligand is coupled to CnBr-activated Sepharose® 4B as the matrix material.

The hvWF-cp or fragments thereof can be obtained using: (i) recombinant gene technology, or (ii) purification procedures starting from e.g., plasma of whole blood, optionally combined with cleaving steps of the purified hvWF-cp from plasma, yielding desired fragments. Preferably, recombinant hvWF-cp ("rhvWF-cp") or the fragments thereof are used in the adsorbent of the present invention.

A number of different vectors can be used for the preparation of rhvWF-cp, including eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD etc. Examples of vectors for eukaryotic expression include: (i) for expression in yeast, vectors such as pAO, pPIC, pYES, pMET etc., using promoters such as AOX1, GAP, GAL1, AUG1 etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses etc., using promoters such as CMV, SV40, EF-1α, UbC, RSV, ADV, BPV, β-Ac, etc.

The host cells, i.e., prokaryotic or eukaryotic systems, used for expression of rhvWF-cp or fragments thereof depend on the expression vector being introduced into the host cells, and may be bacteria cells (e.g., *E. coli, B. subtilis*); or eukaryotic cells such as yeast cells, (e.g., *Pichia* strains); insect cells (e.g. Sf9, Sf 21, High Five, and S2); and mammalian cells (e.g., Vero, MRC5, CHO, COS, 3T3, HEK 293, BHK, SK-Hep, HepG2, CV-1, and Hela).

In one embodiment of the present invention, the fragments of rhvWF-cp are selected from the group consisting of SEQ ID NOs:1-5.

In one preferred embodiment of the present invention, the recombinant fragments of vWF-cp can be prepared by expression in *E. coli* as follows:

Fragments of rhvWF-cp are generated by PCR and cloned into a suitable expression vector such as the vector pRSET-B (Invitrogen).

Figure 4:
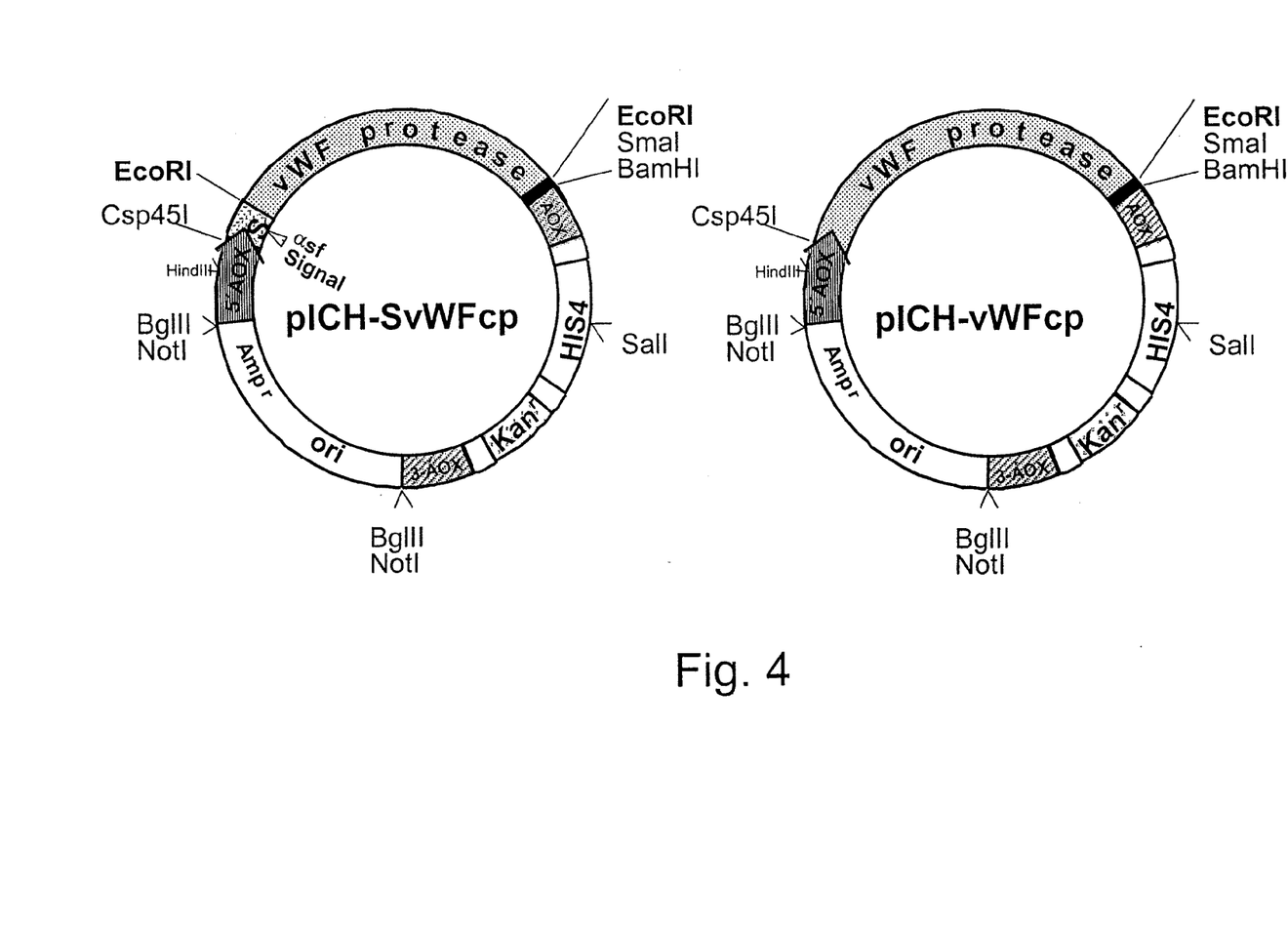
FIG. 4 shows expression plasmids pICHvWFcp and pICH-SvWFcp containing recombinant hvWF-cp fragments for inducible expression in Pichia pastoris.

Using the full length cDNA clone disclosed in WO 02/42442 as a template, fragments containing different fragments of the gene of the mature protein are generated by PCR using the following primer combinations:

*toris*. Here, the complete gene of the rhvWFcp (without propeptide) or fragments thereof are cloned into suitable *Pichia pastoris* expression vectors (e.g., pICHJ-43839), as a Csp451-EcoR1 fragment. Alternatively the gene or fragments are cloned behind the yeast alpha-secretion factor signal of the vector pICH-S 43465 as EcoRI cassettes. The signal sequence allows secretion of the protein into the supernatant (FIG. 4).

The plasmids are grown under standard conditions in *E. coli* and transformed into the *Pichia* strain GS115 by electroporation. The plasmids are either integrated into the His-4 locus after linearization with SalI or into the AOX locus after removal of the *E. coli* specific cassette with Not1. Amplification of the inserts is possible by G418 selection. The gene of interest is expressed after induction of the AOX promoter by methanol.

In another embodiment of the present invention, the fragments to be used as affinity ligands are peptides having amino acid sequences contained in the hvWF-cp and preferably having a length in the range of from about 6 to 30 amino acids, more preferably from about 6 to about 20 amino acids. One advantage of using such peptides as affinity ligands in the adsorbent of the present invention is the increase in the capacity of the adsorbent. This results in a reduction of time for a patient being subjected a selective removal of anti-vWF-cp-abs from whole blood.

| Name of primer | Sequence | Orientation | SEQ ID NO: |
|---|---|---|---|
| pPCR.FURLAN-6699 | GCCTTACTCGAGGGCTGCAGGCGGCGGCATCC | DIR | 6 |
| pPCR.FURLAN-6700 | CGAGGAATTCACACGTGTCCGCTGGGGCCG | REV | 7 |
| pPCR.FURLAN-6740 | GCCTTACTCGAGCAGCGGACACGTGATGGCTTC | DIR | 8 |
| pPCR.FURLAN-6741 | CGAGGAATTCAATAGCGCCCTCCGATCCTCAC | REV | 9 |
| pPCR.FURLAN-6742 | GCCTTACTCGATGTCTACATTGCCAACCACA | DIR | 10 |
| pPCR.FURLAN-6743 | CGAGGAATTCACTCTTCCTGGACAGGCACC | REV | 11 |
| pPCR.FURLAN-6744 | GCCTTACTCGAGGGTGCCTGTCCAGGAAGAG | DIR | 12 |
| pPCR.FURLAN-6745 | CGAGGAATTCAAAGCAGCAACATGTCCC | REV | 13 |
| pPCR.FURLAN-6746 | GCCTTACTCGAGGGACATGTTGCTGCTTTGG | DIR | 14 |
| pPCR.FURLAN-6760 | GGCGAATTCTCAGGTTCCTTCCTTTCCCTTC | REV | 15 |

Figure 2:
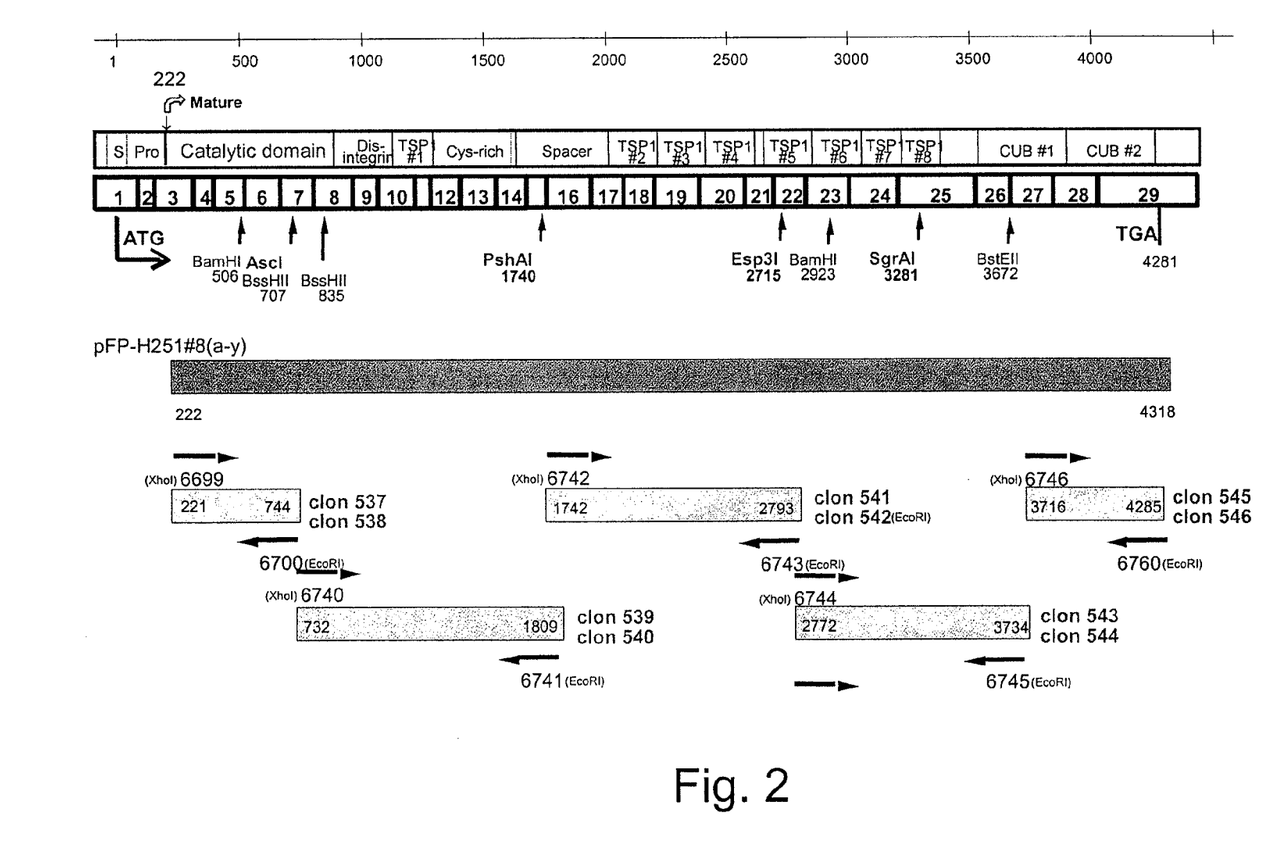
FIG. 2 depicts fragments of the recombinant hvWF-cp cloned into the T7 expression vector pRSET-B.
Figure 3:
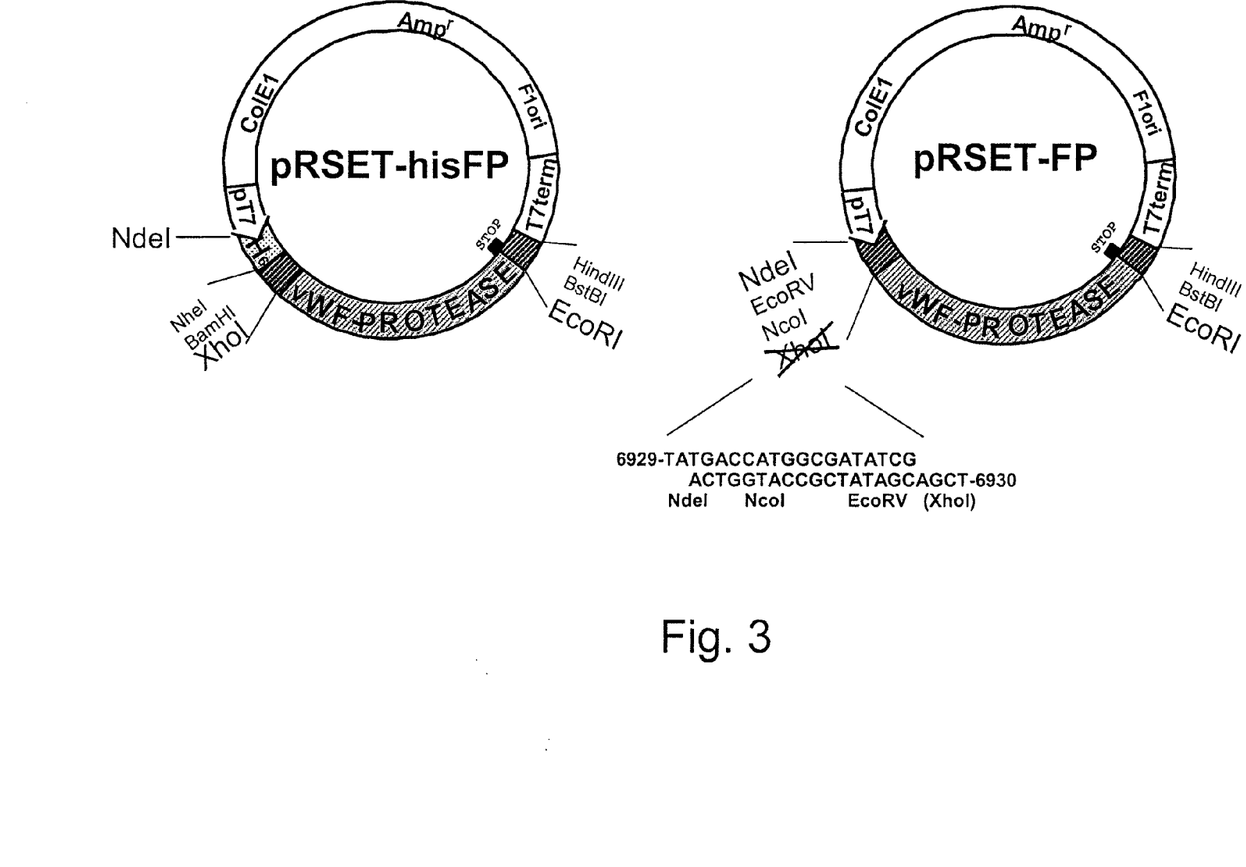
FIG. 3 shows plasmids for inducible expression of recombinant hvWF-cp in E. coli. Proteins containing a His 6 tag can be purified on Ni columns.

The PCR fragments are cut with suitable restriction enzymes such as EcoRI/XhoI and cloned into the vector such as pRSET-B, cleaved with the same enzymes resulting in the desired plasmids such as pRSET-FP537, pRSET-FP539, pRSETFP541, pRSET-FP543, pRSET-FP545 (FIG. 2). The constructs are cloned in two variants, with or without a HIS-6 tag. In the constructs without a HIS-6 tag, the NdeI-XhoI fragment is substituted by the synthetic oligonucleotides o.pRET-FPdHIS(1)-6929 and o.pRSET-FPdHIS(2)-6930 (FIG. 3).

All these plasmids contain the gene of interest under the control of the T7 promoter. The plasmids are transformed into a suitable *E. coli* strain such as JM109. Expression of the protein is induced by infection with, e.g., the M13 mp18/T7 coding for the T7 polymerase under the control of the pLac promoter. The advantage of this system is the extremely tight regulation of expression which is important if the protein is toxic to the cells.

Another embodiment is the generation of recombinant rhvWF-cp or fragments thereof by expression in *Pichia pas-*

The hvWF-cp or the fragments thereof which either have been prepared using recombinant gene technology, or have been purified from plasma of whole blood, have at least one functionally active epitope directed to anti-vWF-cp-abs under physiological conditions. The term "physiological conditions" means an artificial environment which mimics on the one hand the natural environment of the blood circulating system in man, and on the other hand provides an environment suitable for antibody-antigen-binding. In a preferred embodiment, the term "physiological conditions" includes buffer-systems such as PBS (pH 7.3) for carrying out such binding. The term "functionally active epitope" means an antigenic determinant capable of binding one anti-vWF-cp-ab under the above-defined physiological conditions.

In the method for selective removal of anti-vWF-cp-abs from human plasma, the provision of plasma from whole blood of a patient having a disorder associated with occurrence of anti-vWF-cp-abs can be carried out by any method known in the art. Examples include plasmaphareses.

In step (b) of the method of the present invention, the plasma is typically diluted in binding buffer such as PBS (pH 7.3), and applied to the above-defined adsorbent which is already equilibrated in binding buffer.

After step (c), the adsorbent can be regenerated by diluting the bound anti-vWF-cp-abs using a regeneration buffer such as 50% (v/v) ethylene glycol followed by 50 mM glycine/150 mM NaCl (pH 3.0). The adsorbent is then re-equilibrated in storage buffer such as binding buffer containing 0.05% $NaN_3$.

All chromatographic steps are preferably performed at a temperature of about <room temperature, preferably at about 4° C., with e.g., a linear flow rate ranging from e.g., about 10 to about 60 cm/hrs.

The method of the present invention can be used for treating a patient having a disorder associated with occurrence of anti-vWF-cp-abs such as a thromboembolic disease. Examples of thromboembolic diseases include thrombotic thrombocytopenic purpura, Henoch-Schönlein purpura, preeclampsia, neonatal thrombocytopenia or hemolytic-uremic syndrome. This includes also medicament-associated formation of anti-vWF-cp-abs in man.

The present invention will now be further illustrated in the following examples, without being limited thereto.

Example 1

Ligand Coupling

The fragment pRSET-FP 537 (SEQ ID NO:1) of rhvWF-CP is recombinantly expressed in *E. coli*, IM 109 purified and coupled as affinity ligand to CNBr-activated Sepharose® 4B (Amersham Pharmacia Biotech, Uppsala, Sweden) following the procedure of the suppliers protocol. The resulting affinity matrix (fragment FP 537 (SEQ ID NO:1) of rhvWF-cp/Sepharose® 4B) is used to specifically capture and remove anti-vWF-cp-abs out of human patient plasma, which inhibit endogenous vWF-cp activity.

Example 2

Affinity Chromatography

Human plasma is diluted in binding buffer (PBS pH 7.3) and applied to the equilibrated fragment FP 537 (SEQ ID NO:1) of rhvWF-cp/Sepharose® 4B as affinity matrix to allow selective immunadsorption of vWF-cp-abs to the fragment FP 537 (SEQ ID NO:1) of rhvWF-cp as affinity ligand. The flow-through consisting of the unadsorbed plasma fraction is collected and analyzed for its selective depletion of anti-vWF-cp-abs. Captured antibodies are recovered by 50% ethylene glycol elution following 50 mM glycine/150 mM NaCl, pH 3.0 for complete regeneration of the affinity matrix. After re-equilibration with binding buffer the column is stored in binding buffer containing 0.05% $NaN_3$. All chromatographic steps are performed at 4° C. with a linear flow rate of 10-60 cm/hrs. The collected fractions are analyzed for vWF-cp activity inhibiting antibodies to monitor the efficiency of the immunadsorption.

Example 3

Assay of vWF-cp Activity in the Presence of Inhibiting Antibodies

Figure 1:
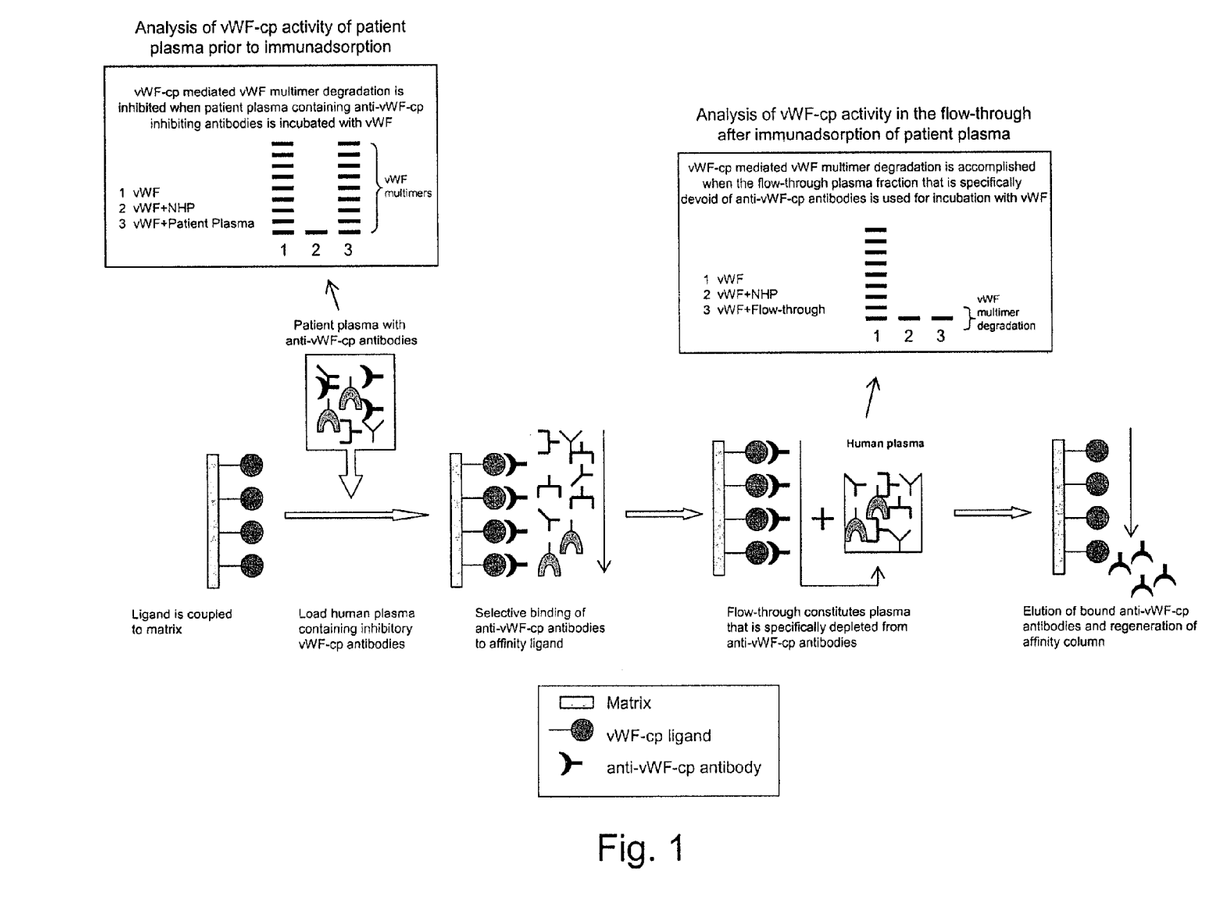
FIG. 1 is a schematic illustration of the immunadsorption procedure of anti-vWF-cp-abs from patient's plasma using hvWF-cp or fragments thereof as an affinity ligand coupled to a matrix.

The activity of vWF-cp after incubation with samples containing vWF-cp activity inhibiting antibodies and fractions thereof collected following the immunadsorption is determined at low ionic strength and in the presence of urea as described in Furlan et al., 1996, supra. A pool of normal human plasma (NHP, Baxter AG) is incubated with the samples for 10 minutes at 37° C. in various ratios in a total volume of 10 µl. The mixture is then diluted to 100 µl in 0.15 M NaCl, 10 mM Tris, pH 7.4, 1 mM Pefabloc SC containing 10 mM $BaCl_2$ and incubated for 5 minutes at 37° C. The incubation mixture is immediately added to 50 µl of plasma-derived vWF (50 µg/ml) (Stago, Parsippany, N.J.) and transferred onto circular dialysis membranes (VSWP, 25 mm diameter, Millipore) floating on 50 ml 1.5 M urea/5 mM Tris, pH 8.0. Overnight incubation at 37° C. is stopped by the addition of 10 µl 0.2 M EDTA, pH 7.4. Dilutions of NHP without previous incubation with inhibiting antibodies is used for vWF-cp activity calibration. For the analysis of vWF multimers approximately 25 ng vWF per lane was subjected to non-reducing SDS-1% agarose gels and detected with rabbit anti-vWF antibodies (Dakopatts, Copenhagen, Denmark) and alkaline phosphatase conjugated goat anti-rabbit IgG antibodies (Promega, Madison, Wis.). The procedural steps of this example are illustrated in FIG. 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

We claim:

1. An adsorbent for selective removal of anti-von Willebrand Factor cleaving protease antibodies from human plasma, wherein the adsorbent comprise a human von-Willebrand Factor-cleaving protease fragment that consists of amino acid sequence SEQ ID NO:1, SEQ ID NO:2, SEQ ID NO:3, SEQ ID NO:4 or SEQ ID NO:5 chemically coupled to an inert matrix material.

2. The adsorbent according to claim 1, wherein said fragment is a recombinant fragment.

3. The adsorbent according to claim 1, wherein said matrix material is selected form the group consisting of carbohydrates, silicates, glasses and organic polyreaction products.

4. The adsorbent according to claim 3, wherein said carbohydrates comprise cross-linked modified agarose.

5. The adsorbent according to claim 1, wherein said matrix material is present in the form of porous beads.

6. The adsorbent according to claim 1, wherein said fragment is coupled directly or indirectly via a spacer to said matrix material.

7. A method for selective removal of anti-von Willebrand Factor-cleaving protease antibodies from human plasma, comprising the steps of: (a) providing a plasma from whole blood from a patient having a disorder associated with occurrence of anti-von Willebrand Factor-cleaving protease antibodies; (b) subjecting said plasma to an affinity chromatography using an adsorbent comprising a human von-Willebrand Factor-cleaving protease fragment that consists of amino acid sequence SEQ ID NO:1, SEQ ID NO:2, SEQ ID NO:3, SEQ ID NO:4 or SEQ ID NO:5 chemically coupled to an inert matrix material; wherein the affinity chromatography is performed under physiological conditions in which the antibodies bind to human von Willebrand Factor-cleaving protease; and (c) collecting a flow-through fraction which is essentially devoid of anti-von Willebrand Factor-cleaving protease antibodies.

8. The method of claim 7, wherein said fragment is a recombinant fragment.

9. The method according to claim 7, wherein PBS is a binding buffer in step (b).

10. The method according to claim 7, wherein the adsorbent is regenerated by eluting the bound antibodies and re-equilibrating in PBS.

11. The method according to claim 7, wherein the disorder is a thromboembolic disease.

12. The method according to claim 11, wherein the thromboembolic disease is selected from the group consisting of thrombotic thrombocytic purpua, Henoch-Schonlein pupura, preeclampsia, and neonatal thrombocytopenia.

13. The method according to claim 7, wherein said matrix material is selected form the group consisting of carbohydrates, silicates, glasses and organic polyreaction products.

14. The method according to claim 13, wherein said carbohydrates comprise cross-linked modified agarose.

15. The method according to claim 7, wherein said matrix material is present in the form of porous beads.

* * * * *

SEQUENCE LISTING

```
<160> NUMBER OF SEQ ID NOS: 5

<210> SEQ ID NO 1
<211> LENGTH: 175
<212> TYPE: PRT
<213> ORGANISM: human
<220> FEATURE:
<221> NAME/KEY: misc_feature
<223> OTHER INFORMATION: Sequence name: FP537 (SEQ ID No. 1)

<400> SEQUENCE: 1

Arg Ala Ala Gly Gly Ile Leu His Leu Glu Leu Leu Val Ala Val Gly
 1               5                   10                  15
```

-continued

Pro Asp Val Phe Gln Ala His Gln Glu Asp Thr Glu Arg Tyr Val Leu
            20                  25                  30

Thr Asn Leu Asn Ile Gly Ala Glu Leu Leu Arg Asp Pro Ser Leu Gly
        35                  40                  45

Ala Gln Phe Arg Val His Leu Val Lys Met Val Ile Leu Thr Glu Pro
    50                  55                  60

Glu Gly Ala Pro Asn Ile Thr Ala Asn Leu Thr Ser Ser Leu Leu Ser
65                  70                  75                  80

Val Cys Gly Trp Ser Gln Thr Ile Asn Pro Glu Asp Asp Thr Asp Pro
                85                  90                  95

Gly His Ala Asp Leu Val Leu Tyr Ile Thr Arg Phe Asp Leu Glu Leu
            100                 105                 110

Pro Asp Gly Asn Arg Gln Val Arg Gly Val Thr Gln Leu Gly Gly Ala
        115                 120                 125

Cys Ser Pro Thr Trp Ser Cys Leu Ile Thr Glu Asp Thr Gly Phe Asp
    130                 135                 140

Leu Gly Val Thr Ile Ala His Glu Ile Gly His Ser Phe Gly Leu Glu
145                 150                 155                 160

His Asp Gly Ala Pro Gly Ser Gly Cys Gly Pro Ser Gly His Val
                165                 170                 175

<210> SEQ ID NO 2
<211> LENGTH: 359
<212> TYPE: PRT
<213> ORGANISM: human
<220> FEATURE:
<221> NAME/KEY: misc_feature
<223> OTHER INFORMATION: Sequence name: FP539 (SEQ ID No. 2)

<400> SEQUENCE: 2

Ser Gly His Val Met Ala Ser Asp Gly Ala Ala Pro Arg Ala Gly Leu
1               5                   10                  15

Ala Trp Ser Pro Cys Ser Arg Arg Gln Leu Leu Ser Leu Leu Ser Ala
            20                  25                  30

Gly Arg Ala Arg Cys Val Trp Asp Pro Pro Arg Pro Gln Pro Gly Ser
        35                  40                  45

Ala Gly His Pro Pro Asp Ala Gln Pro Gly Leu Tyr Tyr Ser Ala Asn
    50                  55                  60

Glu Gln Cys Arg Val Ala Phe Gly Pro Lys Ala Val Ala Cys Thr Phe
65                  70                  75                  80

Ala Arg Glu His Leu Asp Met Cys Gln Ala Leu Ser Cys His Thr Asp
                85                  90                  95

Pro Leu Asp Gln Ser Ser Cys Ser Arg Leu Leu Val Pro Leu Leu Asp
            100                 105                 110

Gly Thr Glu Cys Gly Val Glu Lys Trp Cys Ser Lys Gly Arg Cys Arg
        115                 120                 125

Ser Leu Val Glu Leu Thr Pro Ile Ala Ala Val His Gly Arg Trp Ser
145                 135                 140

Ser Trp Gly Pro Arg Ser Pro Cys Ser Arg Ser Cys Gly Gly Gly Val
145                 150                 155                 160

Val Thr Arg Arg Arg Gln Cys Asn Asn Pro Arg Pro Ala Phe Gly Gly
                165                 170                 175

Arg Ala Cys Val Gly Ala Asp Leu Gln Ala Glu Met Cys Asn Thr Gln
            180                 185                 190

Ala Cys Glu Lys Thr Gln Leu Glu Phe Met Ser Gln Gln Cys Ala Arg
        195                 200                 205

```
Thr Asp Gly Gln Pro Leu Arg Ser Ser Pro Gly Gly Ala Ser Phe Tyr
    210                 215                 220

His Trp Gly Ala Ala Val Pro His Ser Gln Gly Asp Ala Leu Cys Arg
225                 230                 235                 240

His Met Cys Arg Ala Ile Gly Glu Ser Phe Ile Met Lys Arg Gly Asp
                245                 250                 255

Ser Phe Leu Asp Gly Thr Arg Cys Met Pro Ser Gly Pro Arg Glu Asp
                260                 265                 270

Gly Thr Leu Ser Leu Cys Val Ser Gly Ser Cys Arg Thr Phe Gly Cys
                275                 280                 285

Asp Gly Arg Met Asp Ser Gln Gln Val Trp Asp Arg Cys Gln Val Cys
            290                 295                 300

Gly Gly Asp Asn Ser Thr Cys Ser Pro Arg Lys Gly Ser Phe Thr Ala
305                 310                 315                 320

Gly Arg Ala Arg Glu Tyr Val Thr Phe Leu Thr Val Thr Pro Asn Leu
                325                 330                 335

Thr Ser Val Tyr Ile Ala Asn His Arg Pro Leu Phe Thr His Leu Ala
                340                 345                 350

Val Arg Ile Gly Gly Arg Tyr
            355
```

<210> SEQ ID NO 3
<211> LENGTH: 350
<212> TYPE: PRT
<213> ORGANISM: human
<220> FEATURE:
<221> NAME/KEY: misc_feature
<223> OTHER INFORMATION: Sequence name: FP541 (SEQ ID No. 3)

<400> SEQUENCE: 3

```
Ser Val Tyr Ile Ala Asn His Arg Pro Leu Phe Thr His Leu Ala Val
1               5                   10                  15

Arg Ile Gly Gly Arg Tyr Val Val Ala Gly Lys Met Ser Ile Ser Pro
                20                  25                  30

Asn Thr Thr Tyr Pro Ser Leu Leu Glu Asp Gly Arg Val Glu Tyr Arg
                35                  40                  45

Val Ala Leu Thr Glu Asp Arg Leu Pro Arg Leu Glu Glu Ile Arg Ile
    50                  55                  60

Trp Gly Pro Leu Gln Glu Asp Ala Asp Ile Gln Val Tyr Arg Arg Tyr
65                  70                  75                  80

Gly Glu Glu Tyr Gly Asn Leu Thr Arg Pro Asp Ile Thr Phe Thr Tyr
                85                  90                  95

Phe Gln Pro Lys Pro Arg Gln Ala Trp Val Trp Ala Ala Val Arg Gly
                100                 105                 110

Pro Cys Ser Val Ser Cys Gly Ala Gly Leu Arg Trp Val Asn Tyr Ser
                115                 120                 125

Cys Leu Asp Gln Ala Arg Lys Glu Leu Val Glu Thr Val Gln Cys Gln
            130                 135                 140

Gly Ser Gln Gln Pro Pro Ala Trp Pro Glu Ala Cys Val Leu Glu Pro
145                 150                 155                 160

Cys Pro Pro Tyr Trp Ala Val Gly Asp Phe Gly Pro Cys Ser Ala Ser
                165                 170                 175

Cys Gly Gly Gly Leu Arg Glu Arg Pro Val Arg Cys Val Glu Ala Gln
                180                 185                 190

Gly Ser Leu Leu Lys Thr Leu Pro Pro Ala Arg Cys Arg Ala Gly Ala
```

```
                    195                 200                 205
Gln Gln Pro Ala Val Ala Leu Glu Thr Cys Asn Pro Gln Pro Cys Pro
    210                 215                 220

Ala Arg Trp Glu Val Ser Glu Pro Ser Ser Cys Thr Ser Ala Gly Gly
225                 230                 235                 240

Ala Gly Leu Ala Leu Glu Asn Glu Thr Cys Val Pro Gly Ala Asp Gly
                245                 250                 255

Leu Glu Ala Pro Val Thr Glu Gly Pro Gly Ser Val Asp Glu Lys Leu
            260                 265                 270

Pro Ala Pro Glu Pro Cys Val Gly Met Ser Cys Pro Pro Gly Trp Gly
        275                 280                 285

His Leu Asp Ala Thr Ser Ala Gly Glu Lys Ala Pro Ser Pro Trp Gly
    290                 295                 300

Ser Ile Arg Thr Gly Ala Gln Ala Ala His Val Trp Thr Pro Ala Ala
305                 310                 315                 320

Gly Ser Cys Ser Val Ser Cys Gly Arg Gly Leu Met Glu Leu Arg Phe
                325                 330                 335

Leu Cys Met Asp Ser Ala Leu Arg Val Pro Val Gln Glu Glu
            340                 345                 350

<210> SEQ ID NO 4
<211> LENGTH: 320
<212> TYPE: PRT
<213> ORGANISM: human
<220> FEATURE:
<221> NAME/KEY: misc_feature
<223> OTHER INFORMATION: Sequence: FP543 (SEQ ID No. 4)

<400> SEQUENCE: 4

Arg Val Pro Val Gln Glu Glu Leu Cys Gly Leu Ala Ser Lys Pro Gly
1               5                   10                  15

Ser Arg Arg Glu Val Cys Gln Ala Val Pro Cys Pro Ala Arg Trp Gln
            20                  25                  30

Tyr Lys Leu Ala Ala Cys Ser Val Ser Cys Gly Arg Gly Val Val Arg
        35                  40                  45

Arg Ile Leu Tyr Cys Ala Arg Ala His Gly Glu Asp Asp Gly Glu Glu
    50                  55                  60

Ile Leu Leu Asp Thr Gln Cys Gln Gly Leu Pro Arg Pro Glu Pro Gln
65                  70                  75                  80

Glu Ala Cys Ser Leu Glu Pro Cys Pro Pro Arg Trp Lys Val Met Ser
                85                  90                  95

Leu Gly Pro Cys Ser Ala Ser Cys Gly Leu Gly Thr Ala Arg Arg Ser
            100                 105                 110

Val Ala Cys Val Gln Leu Asp Gln Gly Gln Asp Val Glu Val Asp Glu
        115                 120                 125

Ala Ala Cys Ala Ala Leu Val Arg Pro Glu Ala Ser Val Pro Cys Leu
    130                 135                 140

Ile Ala Asp Cys Thr Tyr Arg Trp His Val Gly Thr Trp Met Glu Cys
145                 150                 155                 160

Ser Val Ser Cys Gly Asp Gly Ile Gln Arg Arg Arg Asp Thr Cys Leu
                165                 170                 175

Gly Pro Gln Ala Gln Ala Pro Val Pro Ala Asp Phe Cys Gln His Leu
            180                 185                 190

Pro Lys Pro Val Thr Val Arg Gly Cys Trp Ala Gly Pro Cys Val Gly
        195                 200                 205
```

```
Gln Gly Thr Pro Ser Leu Val Pro His Glu Ala Ala Pro Gly
    210                 215                 220

Arg Thr Thr Ala Thr Pro Ala Gly Ala Ser Leu Glu Trp Ser Gln Ala
225                 230                 235                 240

Arg Gly Leu Leu Phe Ser Pro Ala Pro Gln Pro Arg Arg Leu Leu Pro
                245                 250                 255

Gly Pro Gln Glu Asn Ser Val Gln Ser Ser Ala Cys Gly Arg Gln His
                260                 265                 270

Leu Glu Pro Thr Gly Thr Ile Asp Met Arg Gly Pro Gly Gln Ala Asp
                275                 280                 285

Cys Ala Val Ala Ile Gly Arg Pro Leu Gly Glu Val Val Thr Leu Arg
290                 295                 300

Val Leu Glu Ser Ser Leu Asn Cys Ser Ala Gly Asp Met Leu Leu Leu
305                 310                 315                 320

<210> SEQ ID NO 5
<211> LENGTH: 188
<212> TYPE: PRT
<213> ORGANISM: human
<220> FEATURE:
<221> NAME/KEY: misc_feature
<223> OTHER INFORMATION: Sequence name: FP545 (SEQ ID No. 5)

<400> SEQUENCE: 5

Asp Met Leu Leu Leu Trp Gly Arg Leu Thr Trp Arg Lys Met Cys Arg
1               5                   10                  15

Lys Leu Leu Asp Met Ala Phe Ser Ser Lys Thr Asn Thr Leu Val Val
                20                  25                  30

Arg Gln Arg Cys Gly Arg Pro Gly Gly Gly Val Leu Leu Arg Tyr Gly
            35                  40                  45

Ser Gln Leu Ala Pro Glu Thr Phe Tyr Arg Glu Cys Asp Met Gln Leu
    50                  55                  60

Phe Gly Pro Trp Gly Glu Ile Val Ser Pro Ser Leu Ser Pro Ala Thr
65                  70                  75                  80

Ser Asn Ala Gly Gly Cys Arg Leu Phe Ile Asn Val Ala Pro His Ala
                85                  90                  95

Arg Ile Ala Ile His Ala Leu Ala Thr Asn Met Gly Ala Gly Thr Glu
            100                 105                 110

Gly Ala Asn Ala Ser Tyr Ile Leu Ile Arg Asp Thr His Ser Leu Arg
        115                 120                 125

Thr Thr Ala Phe His Gly Gln Gln Val Leu Tyr Trp Glu Ser Glu Ser
    130                 135                 140

Ser Gln Ala Glu Met Glu Phe Ser Glu Gly Phe Leu Lys Ala Gln Ala
145                 150                 155                 160

Ser Leu Arg Gly Gln Tyr Trp Thr Leu Gln Ser Trp Val Pro Glu Met
                165                 170                 175

Gln Asp Pro Gln Ser Trp Lys Gly Lys Glu Gly Thr
            180                 185
```